(12) United States Patent
Liprie (10) Patent No.: US 6,770,058 B1
(45) Date of Patent: *Aug. 3, 2004

(54) TREATMENT CATHETER INSERT

(75) Inventor: Samuel F. Liprie, Lake Charles, LA (US)

(73) Assignee: Interventional Therapies, LLC, Westport, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/814,401

(22) Filed: Mar. 11, 1997

(51) Int. Cl.[7] .............................................. A61M 25/00
(52) U.S. Cl. ...................................... 604/264; 600/436
(58) Field of Search ......................... 604/264, 280–283, 604/523, 525, 528, 529, 530, 532–535; 600/433–436, 1–3

(56) References Cited

U.S. PATENT DOCUMENTS

| | | | | |
|---|---|---|---|---|
| 4,385,635 A | | 5/1983 | Ruiz .......................... 128/658 |
| 4,578,061 A | | 3/1986 | Lemelson ................... 604/164 |
| 4,588,395 A | | 5/1986 | Lemelson .................... 604/59 |
| 4,782,834 A | * | 11/1988 | Maguire et al. ............ 128/344 |
| 4,861,520 A | * | 8/1989 | Van't Hooft et al. ....... 252/644 |
| 4,873,983 A | | 10/1989 | Winters ...................... 128/657 |
| 4,882,777 A | * | 11/1989 | Narula ........................ 604/281 |
| 4,884,573 A | | 12/1989 | Wijay et al. ................ 128/344 |
| 4,927,418 A | | 5/1990 | Dake et al. .................. 604/264 |
| 4,932,959 A | | 6/1990 | Horzewski et al. ......... 606/194 |
| 4,976,680 A | | 12/1990 | Hayman et al. ............... 600/7 |
| 5,040,543 A | | 8/1991 | Badera et al. .............. 128/772 |
| 5,112,301 A | | 5/1992 | Fenton, Jr. et al. .......... 604/30 |
| 5,149,330 A | | 9/1992 | Brightbill ................... 604/280 |
| 5,158,553 A | | 10/1992 | Berry et al. ................ 604/248 |

(List continued on next page.)

FOREIGN PATENT DOCUMENTS

| | | |
|---|---|---|
| DE | G 91 02 312.2 | 8/1992 |
| WO | 93/04735 | 3/1993 |
| WO | 96/14898 | 5/1996 |

*Primary Examiner*—Long V. Le
*Assistant Examiner*—Ann Y. Lam
(74) *Attorney, Agent, or Firm*—Cantor Colburn LLP (57) ABSTRACT

There is provided a hollow tubular insert having a closed distal end for use within a treatment catheter of the type, used to perform an angioplasty procedure. The insert is provided to receive and guide a source wire having a radioactive distal portion to a position adjacent a stenotic site within a vessel. The insert generally includes an internal segment positionable within the treatment catheter and an external segment extending proximally from a proximal end of the internal segment. A bore extends from an open proximal end of the external segment to a closed distal end of the internal segment for receipt of the source wire. A first connector is provided between the internal and external segments for securing the insert to the treatment catheter. A second connector is provided to connect the insert to a remote afterloader device.

19 Claims, 7 Drawing Sheets

U.S. PATENT DOCUMENTS

| | | | | |
|---|---|---|---|---|
| 5,163,905 A | | 11/1992 | Don Michael | 604/101 |
| 5,174,302 A | | 12/1992 | Palmer | 128/772 |
| 5,183,455 A | | 2/1993 | Hayman et al. | 600/7 |
| 5,183,470 A | * | 2/1993 | Wettermann | 604/281 |
| 5,199,939 A | | 4/1993 | Dake et al. | 600/3 |
| 5,207,648 A | | 5/1993 | Gross | 604/164 |
| 5,209,730 A | | 5/1993 | Sullivan | 604/96 |
| 5,213,561 A | | 5/1993 | Weinstein et al. | 600/7 |
| 5,215,527 A | | 6/1993 | Beck et al. | 604/164 |
| 5,256,150 A | | 10/1993 | Quiachon et al. | 604/171 |
| 5,267,960 A | | 12/1993 | Hayman et al. | 604/106 |
| 5,295,959 A | | 3/1994 | Gurbel et al. | 604/96 |
| 5,308,356 A | | 5/1994 | Blackshear, Jr. et al. | 606/194 |
| 5,318,587 A | | 6/1994 | Davey | 606/194 |
| 5,357,979 A | * | 10/1994 | Imran | 128/772 |
| 5,370,608 A | | 12/1994 | Sahota et al. | 604/20 |
| 5,386,828 A | | 2/1995 | Owens et al. | 128/653.1 |
| 5,395,333 A | | 3/1995 | Brill | 604/101 |
| 5,395,389 A | | 3/1995 | Patel | 606/194 |
| 5,397,307 A | | 3/1995 | Goodin | 604/96 |
| 5,417,653 A | | 5/1995 | Sahota et al. | 604/20 |
| 5,497,784 A | * | 3/1996 | Imran | 128/772 |
| 5,503,613 A | | 4/1996 | Weinberger | 600/3 |
| 5,540,659 A | | 7/1996 | Teirstein | 604/104 |
| 5,549,554 A | | 8/1996 | Miraki | 604/101 |
| 5,556,389 A | | 9/1996 | Liprie | 604/264 |
| 5,618,266 A | | 4/1997 | Liprie | 604/21 |
| 5,620,438 A | | 4/1997 | Amplatz et al. | 606/10 |
| 5,643,171 A | | 7/1997 | Bradshaw et al. | 600/1 |
| 5,643,231 A | * | 7/1997 | Luire et al. | 604/282 |
| 5,653,683 A | * | 8/1997 | D'Andrea | 604/21 |
| 5,776,100 A | * | 7/1998 | Forman | 604/102 |
| 5,779,669 A | * | 7/1998 | Haissaguerre et al. | 604/95 |
| 5,868,685 A | * | 2/1999 | Powell et al. | 600/585 |

* cited by examiner

TREATMENT CATHETER INSERT

BACKGROUND

1. Technical Field

This disclosure relates generally to surgical apparatus for irradiating tissue after treatment and, more particularly, to a treatment catheter insert for use within a treatment catheter and configured to receive a radioactive source wire.

2. Background of Related Art

Because of certain pathological or physiological conditions, it is often necessary to surgically enlarge a lumen of an organ or vessel of the body. This is particularly true, for example, where a vessel has become constricted or stenosed due to a buildup of plaque on the internal walls of the vessel. One method of opening the constriction involves expanding the constricted portion of the vessel with an angioplasty dilatation balloon. While this is an extremely prevalent procedure, occasionally the vessel walls react to the expansion by producing a proliferation of smooth muscle cell growth which causes the vessel to become constricted or restenosed once again.

Recent developments in the angioplasty field have led to the discovery that by irradiating the vascular tissue after the angioplasty procedure the growth of the cells is significantly inhibited. However, the angioplasty catheter typically has a hollow guide wire lumen that generally runs through the center of the catheter and is open at the distal end. When treating for restenosis by using radioactive sources, such as source wires having a radioactive portion, it is necessary to isolate the radioactive source wire from body fluids thus requiring that whatever lumen the radioactive source wire is positioned in have a closed or sealed distal end.

One solution is to remove the open ended angioplasty catheter and replace it with a treatment catheter having a sealed distal end and capable of receipt of a radioactive source wire or ribbon. One exemplary catheter of this type is disclosed in U.S. Pat. No. 5,556,389 to Liprie.

Alternatively, it would be desirable to provide a closed end treatment insert which can be positioned directly within an angioplasty balloon dilatation catheter or other treatment catheter during a procedure and which is capable of receiving a radioactive source wire therein.

SUMMARY

There is provided a hollow, tubular treatment catheter insert having a closed distal end for use within a treatment catheter of the type used to perform an angioplasty procedure. The insert is dimensioned and configured to receive and guide a source wire having a radioactive distal portion into a position adjacent a stenotic site within the vessel. The insert generally includes an insert in an internal segment positionable within a lumen of the treatment catheter and an external segment which extends proximally from the proximal end of the internal segment. The internal segment and external segment have first and second bores, respectively, which together form a single bore for receipt of a source wire. Preferably, the internal segment has a maximum outside diameter of approximately 0.018 inches and a minimum internal diameter of approximately 0.015 inches. The preferred outer diameter insures the insert will fit within a conventional angioplasty treatment catheter guide wire lumen while the preferred internal diameter is sized sufficiently for receipt of a preferred radioactive source wire. Preferably, radiopaque markers are formed at the distal end of the insert to aid in positioning the insert within the treatment catheter.

A connector is provided in an area adjacent the proximal end of the internal segment and the distal end of the external segment. The connector is provided to secure the insert to the treatment catheter to insure that the internal segment of the insert does not move longitudinally within the treatment catheter once in position. Further, where the internal segment and external segments of the insert are formed separately, the connector may provide means for connecting the internal segment to the external segment.

Additionally, a second connector may be provided at the proximal end of the external segment for connection to an afterloader device. In this manner, the radioactive source wire may be safely stored within the afterloader device and thereafter driven out of the afterloader device to a position within the distal end of the internal segment.

There is also provided a system for performing an angioplasty procedure which includes an angioplasty treatment catheter, a hollow tubular insert having a closed distal end for use within the treatment catheter and a radioactive source wire having a radioactive distal tip. The hollow tubular insert is sized to receive the radioactive source wire therein. Additionally, the system may include an afterloader device engageable with a proximal end of the insert and capable of storing and driving the radioactive source wire through the insert.

There is also provided a method of inhibiting restenosis resulting from an angioplasty procedure which generally comprises the steps of inserting a treatment catheter within a vessel of a patient such that a treatment portion of the catheter is positioned within a constricted portion of the vessel and enlarging the constricted portion of the vessel with the treatment portion of the catheter. The method further includes providing a tubular insert having a closed distal end and a proximal end and inserting the tubular insert within a bore of the treatment catheter such that the closed distal end of the tubular insert is positioned adjacent the now enlarged portion of the vessel. The method further includes the step of inserting a source wire having a radioactive distal end within the tubular insert such that the radioactive distal end is positioned adjacent the enlarged portion of the vessel and maintaining the source wire within the tubular insert for a predetermined time sufficient to inhibit the growth of smooth muscle cells.

Preferably, the method additionally includes the steps of securing the insert to the treatment catheter and securing a proximal end of the insert to an afterloader device. Further, the method may also include the steps of using the afterloader device to drive the source wire within the insert and time the treatment period that the radioactive source wire remains within the insert.

BRIEF DESCRIPTION OF THE DRAWINGS

A preferred embodiment of a treatment catheter insert is described below with reference to the drawings wherein.

DETAILED DESCRIPTION OF THE PREFERRED EMBODIMENTS

Figures 1, 1A:
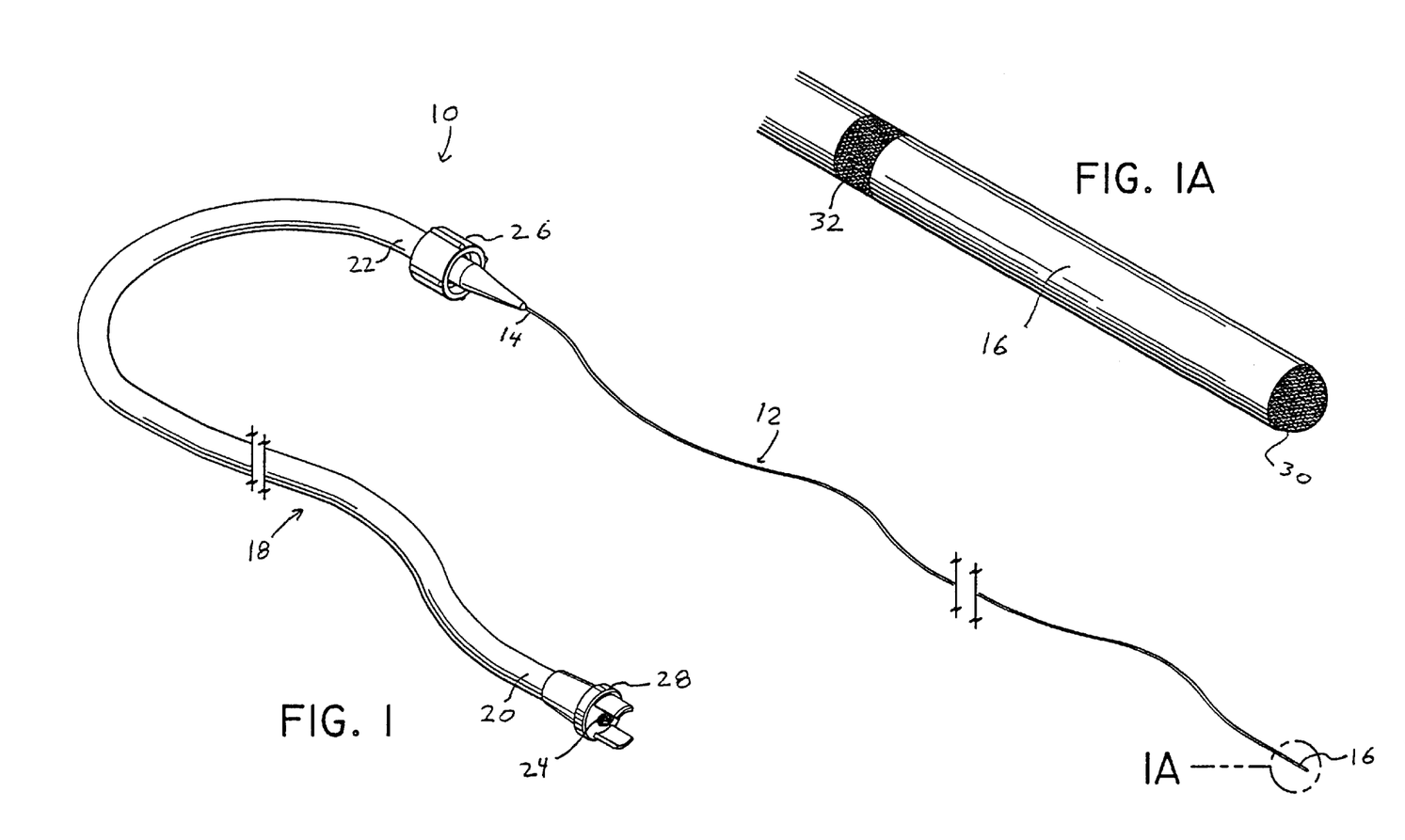
FIG. 1 is a perspective view of a preferred embodiment of a treatment catheter insert.
FIG. 1A is an enlarged view of the area of detail 1A of FIG. 1 and showing the closed distal end of the treatment catheter insert.

With reference now to the drawings wherein like numerals represent like elements throughout the several views and initially with reference to FIG. 1, there is disclosed a preferred embodiment of a treatment catheter insert 10. Insert 10 is provided to be inserted within a treatment catheter, such as, for example, a balloon angioplasty catheter, and provide a closed end lumen or bore for isolation and receipt of a source wire having a radioactive distal end. While the following description details the use of insert 10 within a balloon angioplasty catheter, use within other types of treatment catheters is also contemplated. Insert 10 is formed as a hollow tubular structure and generally includes an internal segment 12 having a proximal end 14 and a distal end 16 and an external segment 18 having a proximal end 20 and a distal end 22. External segment 18 extends proximally from proximal end 14 of internal segment 12. Internal segment 12 is provided to be inserted in a treatment catheter while external segment 18 extends out of the treatment catheter. A bore 24 extends from proximal end 20 of external segment 18 to a point just proximal of distal end 16 to form a sealed closed end lumen through insert 10.

As used herein, the term "distal" refers to that portion of the insert, or component thereof, further from the user while the term "proximal" refers to that portion of the insert, or component thereof, closer to the user.

As noted above, internal segment 12 is configured for insertion in an angioplasty catheter and preferably through a guide wire lumen therein. Thus, internal segment 12 should be flexible enough to follow a torturous and convoluted path through the catheter lumen while being sturdy enough to prevent kinking or internal collapse of bore 24. Preferably, internal segment 12 is formed of a flexible shape memory material, such as, for example, nitinol. Additionally, in order to fit within the catheter lumen and still provide bore 24 with sufficient internal diameter to receive a source wire, internal segment is preferably formed as a thin walled hollow tubular structure with an outer diameter of approximately 0.018 inches. The internal diameter of internal segment 12 is preferably approximately 0.015 inches in diameter to accommodate a source wire of approximately 0.014 inches or less. Thus, sufficient flexibility is obtained with the resultant wall thickness of internal segment being approximately 0.015 inches.

Insert 10 including internal segment 12 and external segment 18 may be formed as a single unitary structure or as separate structures. Where internal segment 12 and external segment 18 are formed as a unitary structure, the preferred material is nitinol. Further, while illustrated as having differing diameters, it is specifically within the contemplated scope of the present disclosure that internal segment 12 and external segment 18 have substantially identical internal and external diameters or variations thereof. Where internal segment 12 and external segment 18 are formed separately and joined to form a single unit, external segment 18 may be formed from various flexible metallic or polymeric materials.

As shown in FIG. 1, a first or intermediate connector 26 is located on insert 10 intermediate, or at the juncture of, proximal end 14 of internal segment 12 and distal end 22 of external segment 18. Intermediate connector 26 is provided to secure insert 10 to a proximal portion of an angioplasty catheter after internal segment 12 has been positioned therein. This connector may be of various types and preferably of the Luer lock variety common in surgical instrumentation. Alternately, O-ring or other types of connectors may be provided. Intermediate connector 26 securely engages corresponding structure on an angioplasty catheter. Additionally, where internal segment 12 and external segment 18 are formed separately, intermediate connector 26 may form structure for coupling these segments together.

The source wire to be used with treatment catheter insert 20 may be loaded into the proximal end 20 of external segment 18 by hand or mechanically. Where the source wire is to be inserted automatically and mechanically, proximal end 20 of external segment 18 may be provided with a second or end connector 28 configured to engage suitable loading structure, such as, for example, an afterloader. Preferably, end connector 28 will include suitable structure to trigger a sensing device provided on the afterloader to signal the afterloader that a secure and proper connection has been made.

Referring now to FIG. 1A, it can be seen that distal end 16 of internal segment 12 is formed with a rounded tip 30 which facilitates routing internal segment 12 through a catheter and provides a plugged or sealed distal end to bore 24. Tip 30 may be formed integrally with distal end 16 or may be formed separately and inserted as a plug into bore 24. Tip 30 may be formed of, or include, radiopaqued material to facilitate positioning distal end 16 within a catheter and adjacent a stenosed region. A second radiopaque marker 32 may be positioned on internal segment 12 proximally of tip 30 to serve as an additional reference for positioning insert 10.

Figure 2:
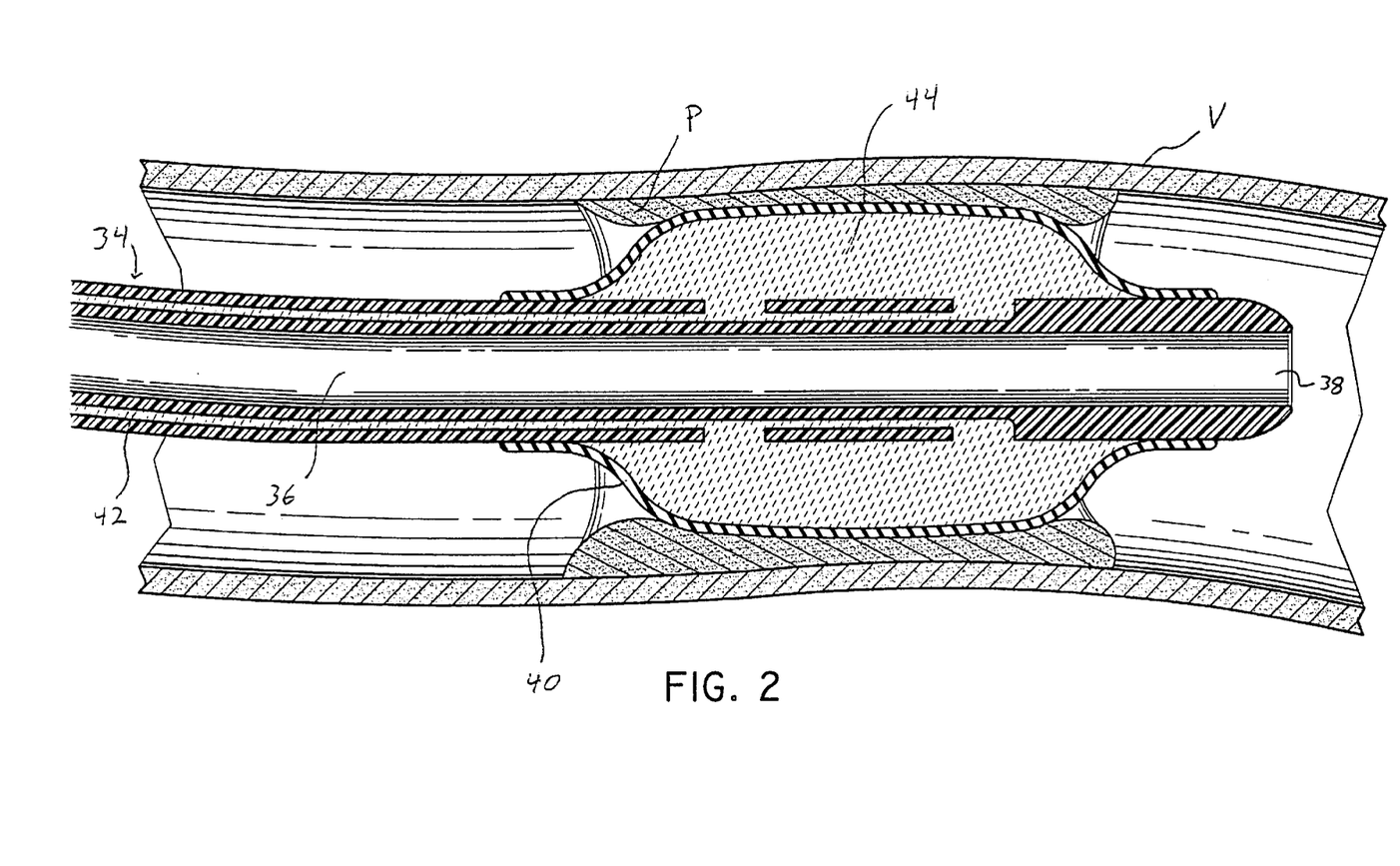
FIG. 2 is a sectional view of a balloon catheter inflated within a stenosed section of a vessel to reduce a constriction.

Referring now to FIG. 2, in use, a conventional balloon angioplasty catheter 34 having a guide wire lumen 36 therethrough and open to a distal end 38 of catheter 34 is inserted into a patient within a vessel V. An expandable dilatation balloon 40, affixed to catheter 34 is positioned within a constricted or stenosed portion P of vessel V caused by the buildup of plaque. Catheter 34 includes an inflation lumen 42 which may be concentric with guidewire lumen 36. Upon infusion of fluid 44 through inflation lumen 42 and into balloon 34, balloon 34 expands to compress plaque P and also stretch the walls of vessel V. It is this stretching or trauma to vessel V that has been found to significantly contribute to the proliferation of smooth tissue growth and thus reconstriction or restenosis of the vessel within a relatively short period following the procedure. As indicated above, the growth of these tissues can be inhibited by application of radioactive treatment after or in conjunction with the angioplasty procedure.

Figure 2B:
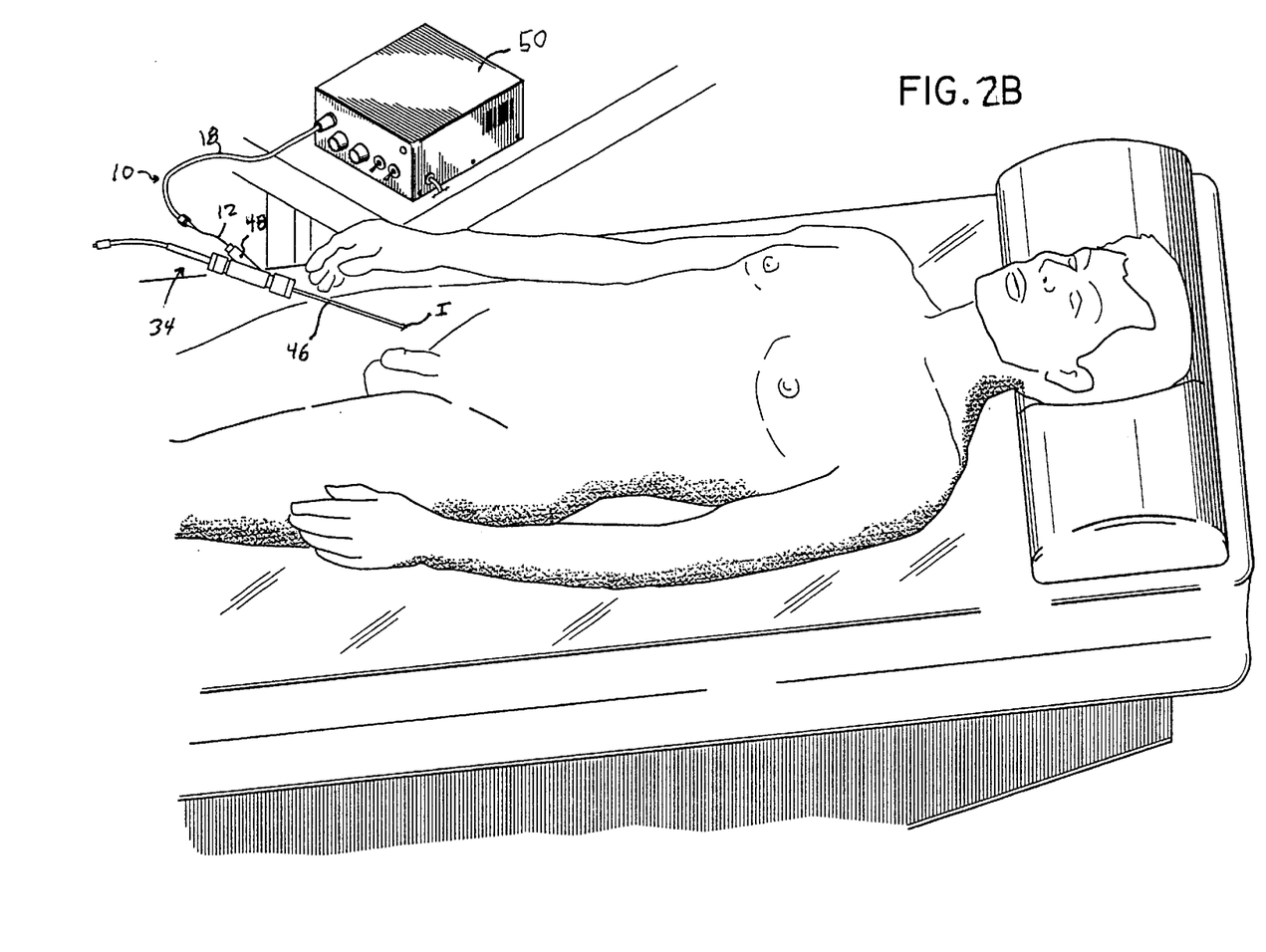
FIG. 2B is a perspective view of a system incorporating the treatment catheter insert of FIG. 1 being positioned in a patient.

Referring now to FIG. 2B, there is shown a proximal end 46 of catheter 34 positioned outside a patient. Catheter 34 extends into the patient through an incision I. Internal segment 12 of insert 10 is inserted through a proximal end 48 of guide wire lumen 36. Insert 10 along with balloon dilatation catheter 34 and a suitable afterloader 50 form a system for performing a complete angioplasty procedure without the need for removal and reinsertion of various devices within the vasculature.

Figures 3, 4:
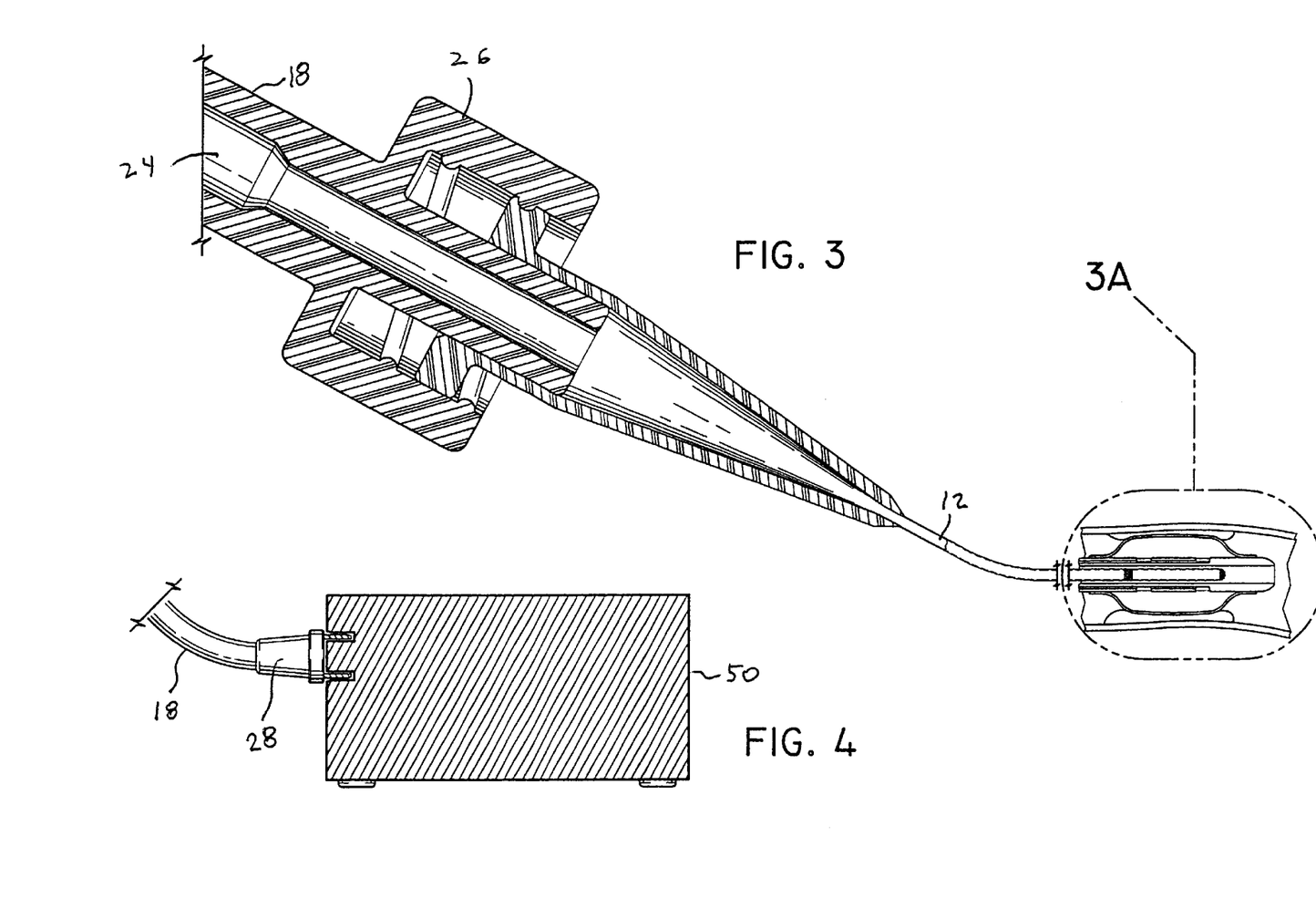
FIG. 3 is a sectional view of a connector portion of the treatment catheter insert used for coupling the insert to an angioplasty catheter.
FIG. 4 is a side view of the proximal end of the treatment catheter insert connected to an afterloader device.
Figure 3A:
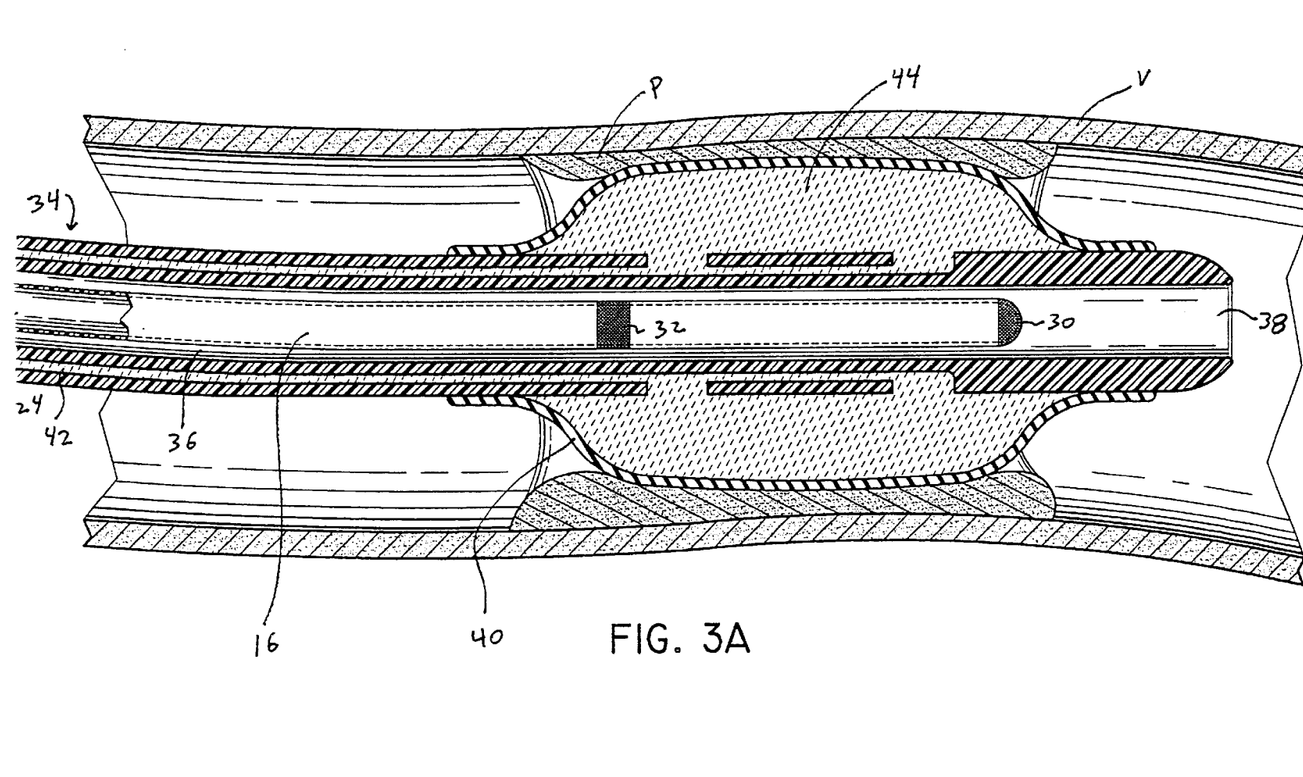
FIG. 3A is an enlarged view of the area of detail 3A of FIG. 3 and showing the distal end of the treatment catheter insert positioned within the balloon catheter of FIG. 2.

As best seen in FIGS. 3 and 3A, internal segment 12 is advanced through guide wire lumen 36 until tip 30 and/or radiopaque marker 32 indicate that distal end 16 of internal segment 12 is properly positioned within balloon catheter 34 and adjacent the stenosed region of vessel V. Additionally, by inserting internal segment 12 within the central guide wire lumen 36, a source 15 wire inserted in insert 10 is automatically centered within catheter 34 and thus within the lumen of a vessel. Once internal segment 12 is inserted into the desired position within guide wire lumen 36, intermediate connector 26 is preferably secured to a corresponding fitting provided on balloon catheter 34. Preferably, the length of internal segment 12 corresponds approximately to the length of guide wire lumen 36.

Referring now to FIGS. 2B and 4, once internal segment 12 of insert 10 has been properly positioned within, and secured to, balloon catheter 34, end connector 28 at proximal end 20 of external segment 18 is connected to afterloader 50. The length of external segment 18 is sized sufficiently to allow insert 10 to be easily connected to afterloader 50. As noted above, afterloader 50 is provided to safely store a source wire having a radioactive distal end and advance the source wire through bore 24 of insert 10 to the proper position within stenosed region. Afterloader 50 additionally may be used to time the period of treatment and retract the source wire from insert 10 at the end of a predetermined period of time or in the event of a malfunction.

Figure 5:
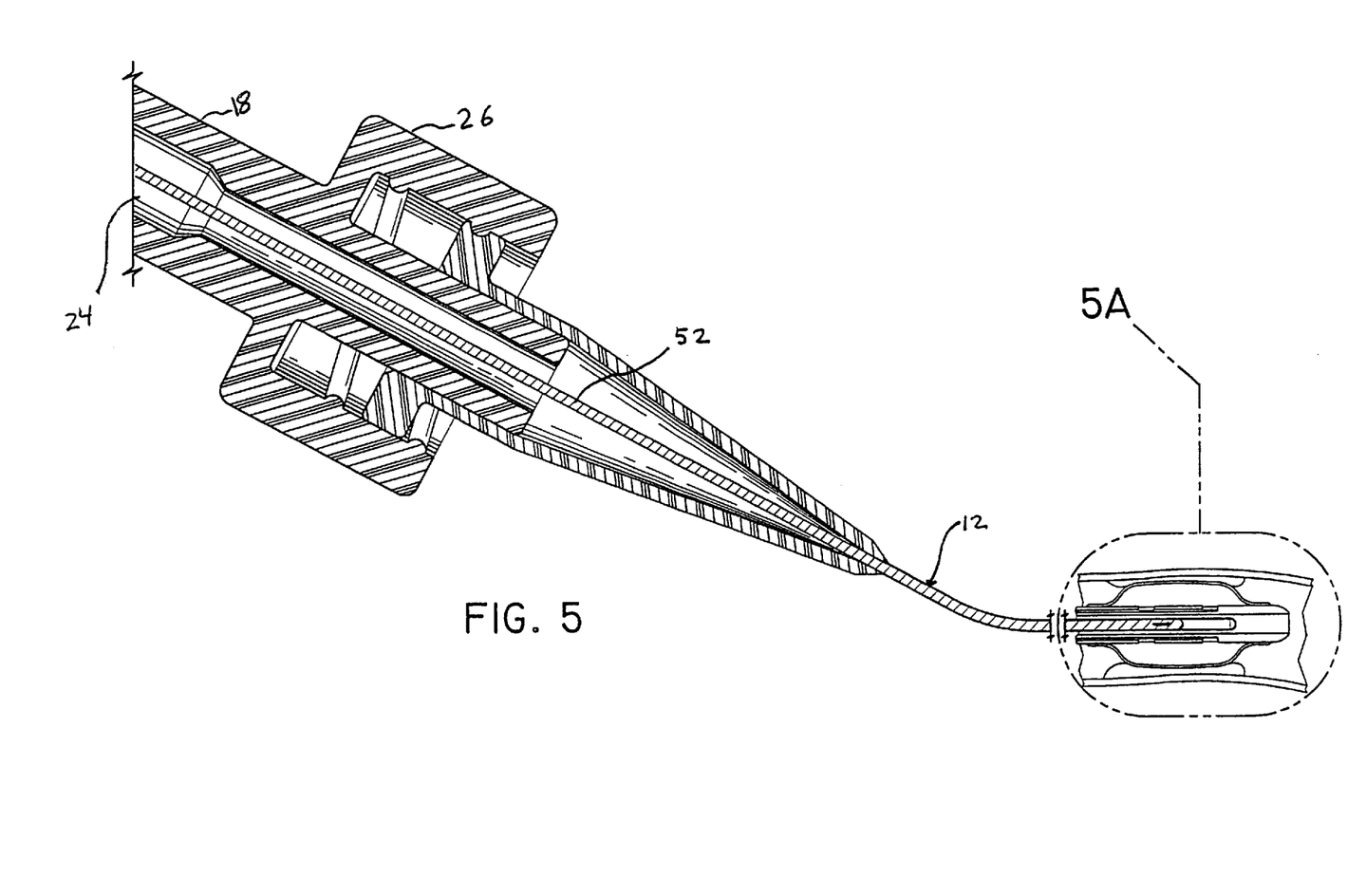
FIG. 5 is a view similar to FIG. 3 and showing a radioactive source wire inserted within the treatment catheter insert.
Figure 5A:
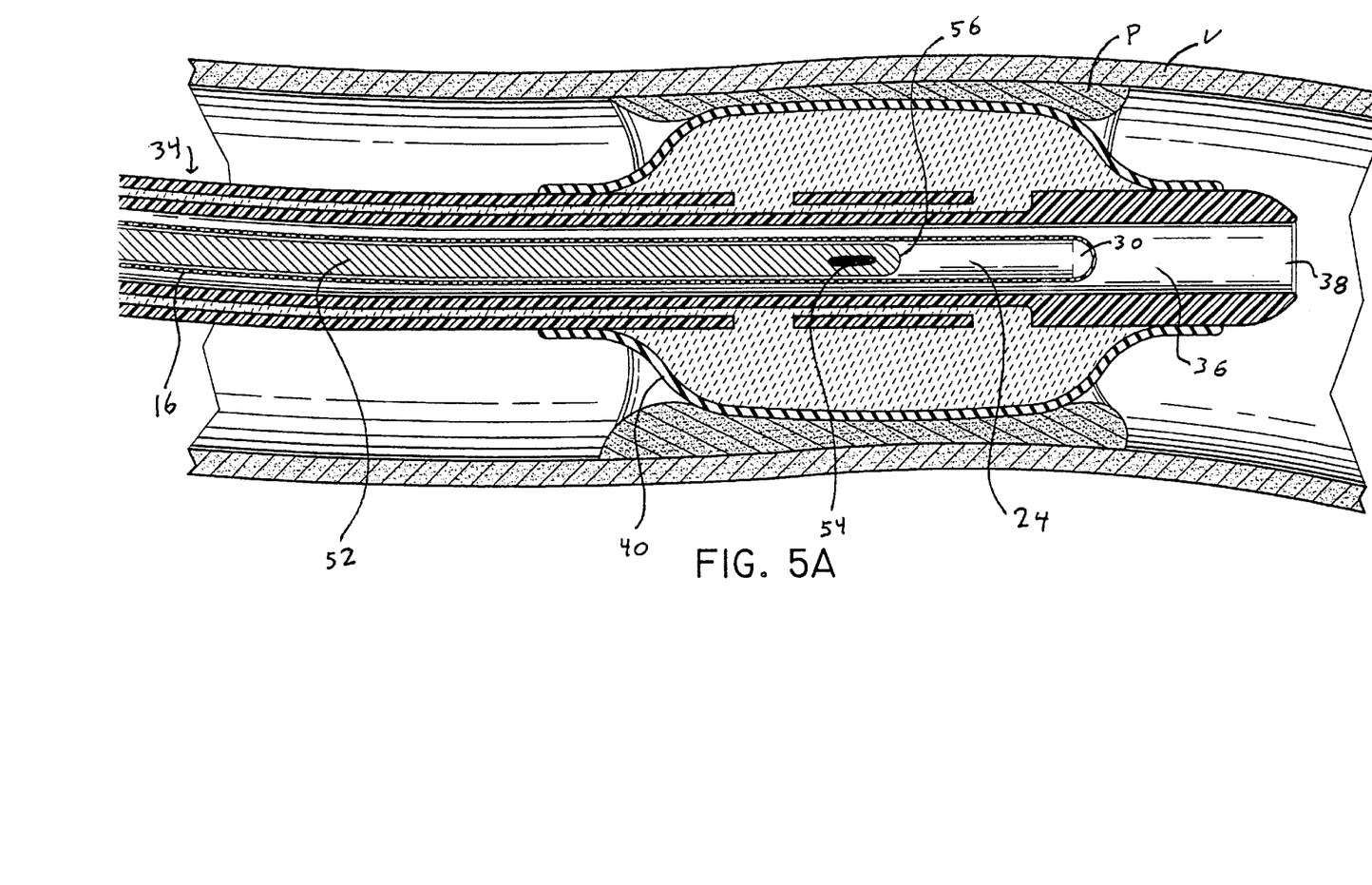
FIG. 5A is an enlarged view of area of detail 5A of FIG. 5 and similar to FIG. 3A showing the radioactive source wire positioned within the treatment catheter insert and adjacent the constricted portion of the vessel.

Referring now to FIGS. 5 and 5A, upon activation of afterloader 50, a source wire 52 having a radioactive portion 54 in a distal end 56 thereof is advanced by afterloader 50 through bore 24 extending through external segment 18 and internal segment 12 until radioactive portion 54 is adjacent the stenosed region. Radioactive portion 54 is maintained at the site for a predetermined period after which it is retracted by afterloader 50. Insert 10 and balloon dilatation catheter 34 may be removed separately or together as a unit.

It will be understood that various modifications may be made to the embodiments disclosed herein. For example, various other types of connectors may be provided to connect the treatment catheter insert to the treatment catheter and to various afterloaders. Additionally, alternative dimensions may be provided to utilize the insert within other treatment structure, such as, for example, prostate catheters, etc.

Therefore, the above description should not be construed as limiting, but merely as exemplifications of preferred embodiments. Those skilled in the art will envision other modifications within the scope and spirit of the claims appended hereto.

What is claimed is:

1. A treatment catheter insert for use within a treatment catheter, comprising:
   a) an internal segment defining a first bore therethrough and having a closed distal end and an open proximal end, the internal segment being dimensioned to traverse the vasculature;
   b) an external segment extending proximally from the internal segment and defining a second bore therethrough, the second bore communicable with the open proximal end of the first bore to form a contiguous main bore; and
   c) a first connector positioned on at least one of the internal and external segments, the connector adapted to engage a portion of a separate treatment catheter extending distally from the first connector.

2. The treatment catheter insert as recited in claim 1, wherein the internal segment is a thin walled tubular member.

3. The treatment catheter insert as recited in claim 2, wherein the tubular member has an internal diameter of approximately 0.015 inches.

4. The treatment catheter insert as recited in claim 2, wherein the tubular member has an outside diameter of approximately 0.018 inches.

5. The treatment catheter insert as recited in claim 1, wherein the internal segment is formed of a flexible, shape memory material.

6. The treatment catheter insert as recited in claim 5, wherein the internal segment is formed of nitinol.

7. The treatment catheter insert as recited in claim 1, wherein the closed distal end of the internal segment forms a rounded tip.

8. The treatment catheter insert as recited in claim 1, further comprising a second connector at a proximal end of the external segment, the second connector engageable with compatible structure on an afterloader device.

9. The treatment catheter insert as recited in claim 1, wherein said insert is dimensioned to receive a source wire having a radioactive distal portion and guide said source wire into a position adjacent a stenotic site within a vessel.

10. The treatment catheter insert as recited in claim 1, wherein said distal end of said internal segment includes at least one radiopaque marker.

11. The treatment catheter insert as recited in claim 1, wherein said internal segment and said external segment are formed as a single unitary structure.

12. The treatment catheter insert as recited in claim 11, wherein said single unitary structure is formed of a flexible, shape memory material.

13. The treatment catheter insert as recited in claim 12, wherein said single unitary structure is formed of nitinol.

14. The treatment catheter insert as recited in claim 1, wherein said closed distal end includes radiopaque material.

15. The treatment catheter insert as recited in claim 1, wherein said internal segment includes a radiopaque marker adjacent to said closed distal end.

16. A treatment catheter insert for use within a treatment catheter comprising:
   a) an internal segment defining a first bore therethrough and having a closed distal end and an open proximal end;
   b) an external segment extending proximally from the internal segment and defining a second bore therethrough, the second bore communicable with the open proximal end of the first bore to form a non-concentric, contiguous main bore; and
   c) a first connector positioned on at least one of the internal and external segments, the first connector includes a Luer lock fitting engageable with a corresponding fitting on a treatment catheter for engaging the treatment catheter and having the treatment catheter extend distally from the first connector, the first connector being remote from the closed distal end and the open proximal end.

17. The treatment catheter insert as recited in claim 16, wherein said first connector includes structure for connecting said internal segment to said external segment.

18. The treatment catheter insert as recited in claim 16, wherein said first connector is located at a junction defined as the location where the external segment extends proximally from the internal segment.

19. A treatment catheter insert for use within a treatment catheter comprising:
  a) an internal segment defining a first bore therethrough and having a closed distal end and an open proximal end;
  b) an external segment extending proximally from the internal segment and defining a second bore therethrough, the second bore communicable with the open proximal end of the first bore;
  c) a first connector positioned on at least one of the internal and external segments, the connector having means for engaging a portion of a treatment catheter; and
  d) a second connector at a proximal end of the external segment, the second connector engageable with compatible structure on an afterloader device, the second connector includes structure to trigger a sensing device provided on the afterloader device to signal the afterloader device that the treatment catheter insert is securely connected to the afterloader device.

* * * * *